(12) United States Patent
Wu et al.

(10) Patent No.: US 7,273,998 B2
(45) Date of Patent: Sep. 25, 2007

(54) SYSTEM AND METHOD FOR MONITORING LASER SHOCK PROCESSING

(75) Inventors: Pingfan Peter Wu, Niskayuna, NY (US); Pamela King Benicewicz, Loudonville, NY (US); Magdi Naim Azer, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 11 days.

(21) Appl. No.: 10/941,560

(22) Filed: Sep. 15, 2004

(65) Prior Publication Data
US 2006/0054607 A1 Mar. 16, 2006

(51) Int. Cl.
*B23K 26/00* (2006.01)
(52) U.S. Cl. .......................... 219/121.62; 219/121.69; 219/121.85
(58) Field of Classification Search ........... 219/121.62, 219/121.69, 121.83, 121.68, 121.85
See application file for complete search history.

(56) References Cited

U.S. PATENT DOCUMENTS

| | | | | |
|---|---|---|---|---|
| 4,968,868 A * | 11/1990 | Aketagawa | ............ | 219/121.68 |
| 5,864,114 A * | 1/1999 | Fukuda | ................... | 219/121.83 |
| 6,002,113 A * | 12/1999 | Alers et al. | .................. | 219/483 |
| 6,075,593 A | 6/2000 | Trantow et al. | ............. | 356/318 |
| 6,554,921 B2 | 4/2003 | Sokol et al. | ................. | 148/508 |
| 6,629,464 B2 * | 10/2003 | Suh et al. | ...................... | 73/602 |
| 6,765,172 B1 * | 7/2004 | Liu et al. | ................ | 219/121.63 |
| 6,897,952 B1 * | 5/2005 | Hagler | ......................... | 356/310 |
| 6,914,215 B2 * | 7/2005 | Davis et al. | ............ | 219/121.85 |
| 2004/0160605 A1 * | 8/2004 | Wang et al. | ................. | 356/437 |
| 2006/0054607 A1 * | 3/2006 | Wu et al. | ............... | 219/121.83 |

\* cited by examiner

*Primary Examiner*—Samuel M. Heinrich
(74) *Attorney, Agent, or Firm*—Fletcher Yoder

(57) ABSTRACT

A method and system for monitoring laser shock peening of a work piece. A line spectrum is obtained from radiation emitted by a plasma produced by a laser shock peening process. The shape of the line spectrum about its emission peak is compared to a defined line shape to verify proper operation of the laser shock peening process. The line shape may be a Lorentzian line shape corresponding to a desired line shape. The line shape may a Gaussian line shape corresponding to an undesired line shape. The system can also detect the failure mode that occurs when the opaque layer is broken through by detecting the plasma spectral component produced by the work piece material, along with the plasma produced by the opaque layer.

16 Claims, 5 Drawing Sheets

SYSTEM AND METHOD FOR MONITORING LASER SHOCK PROCESSING

BACKGROUND

The invention relates generally to process monitoring during laser treatment of a metallic surface, and in particular to real-time monitoring of a laser shock peening process by analyzing laser plasma emissions.

Laser shock peening (LSP), also referred to as laser shock processing, is an effective way of improving fatigue life of a metal work piece. Presently LSP finds wide application in the aerospace and automotive industries as a method for improving the fatigue properties of various metallic components, such as aluminum alloys, steel alloys, titanium based alloys, and nickel based alloys, among others.

Generally, in LSP, a surface of the work piece is covered by an opaque layer and a transparent overlay. The opaque layer may include a black plastic tape or a black paint coated on the surface of the work piece. The transparent overlay generally comprises a layer of water disposed adjacent to the opaque layer. During the process, a high-power pulsed laser beam is focused onto the surface of the work piece. The laser pulse passes through the transparent overlay and is absorbed by the opaque layer, causing a rapid ablation of the opaque layer producing a plasma. The blow-off of the plasma from the surface of the work piece generates a high-amplitude pressure shock wave. The pressure shock wave travels in two directions: First, a compressive wave travels through the opaque layer into the work piece. Second, a shock wave is reflected from the tape and travels backward through the transparent layer. Due to shock impedance mismatch, this backward traveling wave is reflected by the transparent layer toward the work piece. The shock waves ultimately combine to impart plastic strain to the work piece. This results in the deformation of the work piece and imparts compressive residual stresses, which remain following processing. It is these compressive residual stresses in the work piece, which effectively reduce crack propagation rates in the work piece and, thus, improves ftaigue properties of the work piece.

If the pressure produced by the laser is insufficient, the desired changes in mechanical properties of the work piece will not be achieved. Therefore, it is desirable to have the capability of monitoring the pressure and shock wave strength during the LSP process. One approach known in the art involves using a quartz gauge for pressure measurements during laser shock processing. A quartz gauge is based on the piezoelectric behavior of quartz crystals. In this technique, a quartz crystal is disposed on one surface of the work piece to be processed. When a pressure shock wave is applied to a surface of the quartz crystal by a laser pulse, an electric current proportional to the stress difference between the affected surface and the opposite surface is produced by the quartz crystal. The current flows through a resistor and the voltage measured across the resistor is proportional to the pressure response. By analyzing the pressure response of the quartz crystal, it is possible to determine shock-wave pressure produced on the work piece during the actual process. However this approach is disadvantageous because it is indirect and is performed offline, i.e. not in real-time. Moreover, such an approach is expensive, as the quartz crystal needs to be replaced after every laser shot.

Another technique to determine the quality of an LSP process includes performing accelerated fatigue test on a work piece after the work piece has been processed. However, since the LSP process and the work piece material are expensive, it is possible to sample only a limited number of parts for an accelerated fatigue test.

There is, hence, a need for a system and method for monitoring a laser shock peening process, which is inexpensive and is operable substantially in real-time.

BRIEF DESCRIPTION

In one aspect of the present technique, a method of monitoring a laser shock peening process is provided. In accordance with the method, a line spectrum is produced of radiation emitted from a plasma produced by a laser shock peening system. The line spectrum is converted into a signal representative of the line spectrum. The signal representative of the line spectrum is further converted into a graphical representation of the line spectrum, and a curve fit is performed for this graphical representation. A line broadening in the curve fit of the graphical representation of the line spectrum is then compared to a line broadening in the graphical representation of the line spectrum, to establish whether the line spectrum corresponds to a desired line spectrum.

In another aspect, a method of monitoring laser shock peening process is provided. In accordance with the method, a line spectrum is produced of radiation emitted from a plasma produced by the laser shock peening process. At least one of wavelength or frequency of an emission peak in the line spectrum of radiation emitted from the plasma is then compared with at least one of wavelength or frequency of an emission peak in an expected line spectrum of radiation emitted from a material of the work piece, to verify that at least a portion of the laser induced plasma is produced from the work piece material.

In yet another aspect, a laser shock peening system is provided. The system includes a pulsed laser, a spectrometer and a spectrum analyzer. The pulsed laser is operable to direct a pulsed laser beam toward an opaque layer disposed on a surface of a work piece. The spectrometer is operable to produce a line spectrum of radiation emitted by a plasma produced when the pulsed laser strikes the opaque layer. The spectrum analyzer is operable to compare line broadening of the line spectrum about an emission peak with line broadening about a peak in a defined line shape.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in some detail hereinafter, the present technique provides a non-intrusive, real-time monitoring of a laser shock peening process, which is substantially free from environmental influences. The technique described is based on analysis of line broadening of plasma emission during an LSP process, so as to control the quality of every laser shot in real-time.

Figure 1:
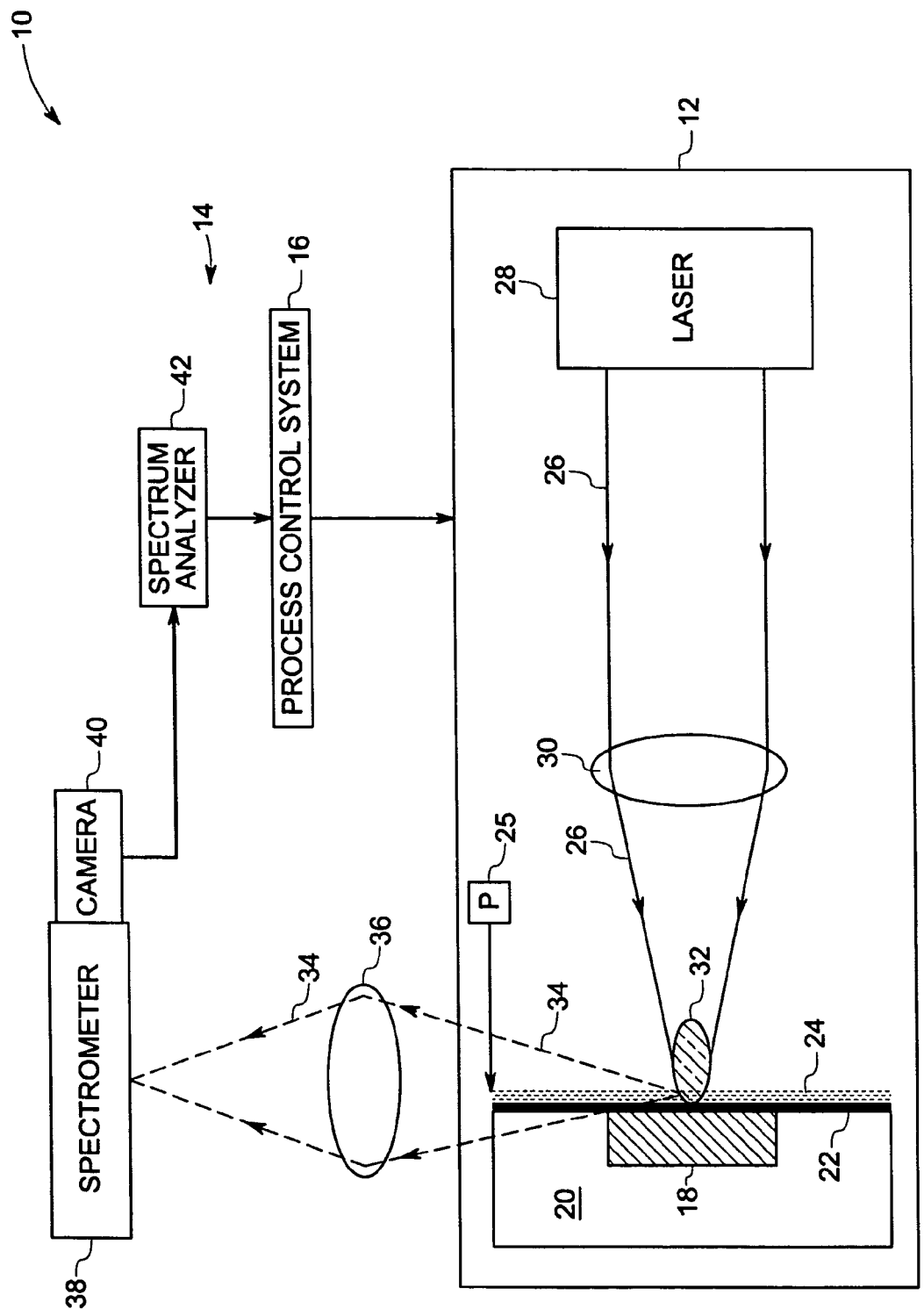
FIG. 1 is a schematic representation of a laser shock peening system according to aspects of the present technique.

Referring now to FIG. 1, a laser shock peening system 10 is illustrated. The illustrated laser shock peening system 10 comprises a laser shock peening unit 12 and a monitoring system 14. The laser shock peening unit 12 is controlled by a process control system 16 that is in communication with the monitoring system 14. The process control system 16 is adapted to adjust process parameters of the laser shock peening unit 12 based upon a signal received from the monitoring system 14.

As illustrated in the figure, the laser shock peening unit 12 comprises a work piece 18 held in position by a holder 20. An opaque overlay 22 and a transparent overlay 24 are applied to one surface of the work piece 18. The opaque overlay 22 may include, for example, a black tape or a black paint coated on one surface of the work piece 18. In this embodiment, the transparent overlay 24 comprises a film of running water delivered, for example, by a flow circulating device 25, such as, a pump. The transparent overlay 24 is disposed adjacent to the opaque overlay 22. However, the transparent overlay 24 may comprise another material, such as a transparent tape. The above-described arrangement may be oriented vertically, or at any desired angle with respect to the vertical.

During the process, a pulsed laser beam 26 is directed from a pulsed laser 28 onto the work piece 18. The laser 28 may comprise, for example, a pulsed Nd:YAG laser or a Nd:Glass laser. However, it is understood that other pulsed lasers may be used to perform laser shock peening. A lens 30 may be used to focus the laser beam 26 onto the work piece 18. The laser beam 26 passes through the transparent layer 24 and is absorbed by the opaque layer 22. The intensity of the focused laser beam causes the opaque layer 22 to vaporize, producing a plasma 32. The temperature at which the opaque layer 22 vaporizes may be on the order of 10,000 K. The plasma expansion is confined substantially by the transparent overlay 24, resulting in a pressure pulse that is reflected from the transparent layer 24 back towards the work piece 18. The pressure pulse caused by this reflected wave superimposes with a forward traveling shock wave produced by an initial ablation of the opaque layer 22 and causes the work piece 18 to deform, which imparts deep compressive stresses within the work piece 18. It has been observed that the magnitude of the pressure pulse is higher when the plasma expansion is confined by a transparent overlay, such as the water layer described above, than without a transparent overlay.

The plasma 32 produced by the vaporization of the opaque layer 22 produces an emission of light 34. According to the present technique, light from these spectral emissions 34, also referred to as plasma emissions, is focused by a lens 36 into an entrance slit of a spectrometer 38. A spectrometer 38 is an instrument for measuring spectral intensity of light at a predefined wavelength range. The spectral emissions 34 are dispersed into their constituent wavelengths by the spectrometer. An image of the spectrum of light produced in the spectrometer 38 is taken by a camera 40. The camera 40 may include a gated-intensified charge-coupled device (CCD), or a complimentary metal oxide semiconductor (CMOS) camera, amongst other image recording devices. The image from the camera 40 is fed to a spectrum analyzer 42 for an analysis of the spectral emissions captured by the image. In one embodiment, the spectrum analyzer 42 is configured to generate a line spectrum of the plasma emission 34 based on light intensity data captured in the image taken by the camera 40. The spectrum analyzer 42 may include, for example, a processing unit, which implements an executable software code. The spectrum analyzer 42 may include a monitor for visual display of results. In one embodiment, the spectrum analyzer is a computer with special data processing software which enables a computer to perform an analysis of the spectral emissions captured by the image from the camera 40.

Figure 2:
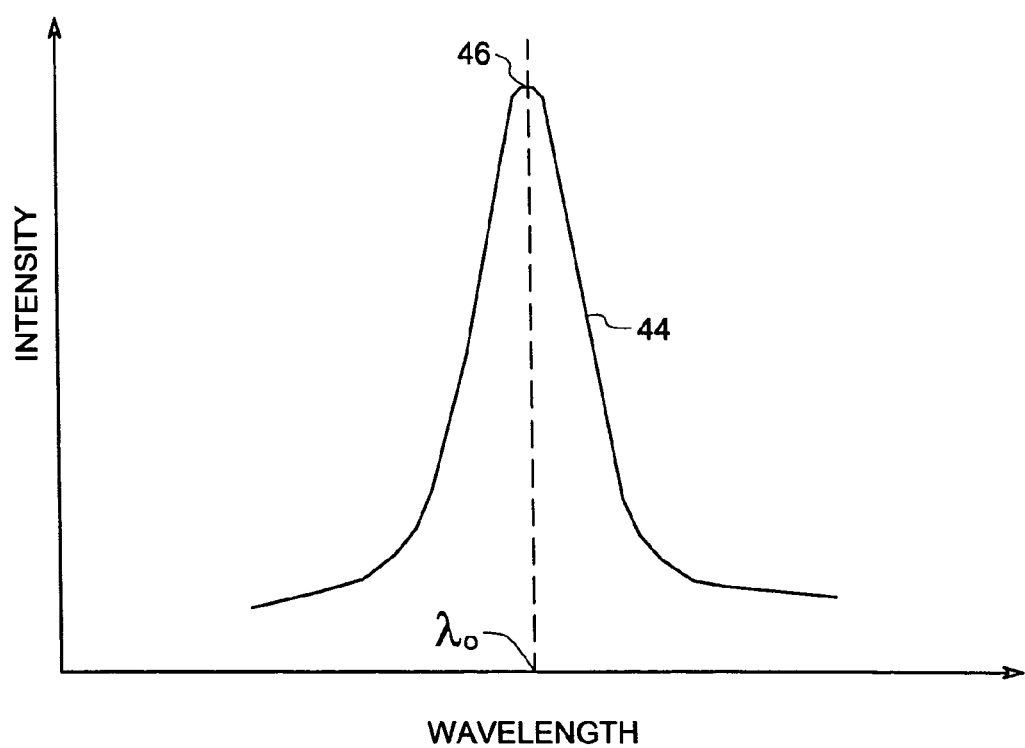
FIG. 2 is a graphical illustration of a representative line spectrum around a specific wavelength $\lambda_0$ of plasma radiation produced in an LSP process.

FIG. 2 illustrates an example of a line spectrum, represented by reference numeral 44, of light received from a plasma produced by a laser shock peening process. The line spectrum 44 has an emission peak 46 at a specific wavelength ($\lambda_o$). However, rather than simply being a straight line at the specific wavelength ($\lambda_o$), the line spectrum 44 has a general bell-shape. The bell-shape of the line spectrum 44 around the emission peak 46 is referred to as line broadening. There are several effects that cause the spectral line to broaden around the spectral peak in a plasma emission, such as: natural broadening, thermal broadening, collisional broadening, and Stark broadening.

Natural line broadening results from the fact that excited levels of atoms have certain mean lives, and these mean lives, by virtue of the Heisenberg's uncertainty principle, imply a spread in the energy values. The spread in energy values of the excited atoms causes light of different wavelengths to be emitted. Natural line broadening generally results in a spectral emission having a Lorentzian line shape. Since an LSP process generally produces line spectra that have lifetimes of hundreds of nanoseconds, natural line broadening is on the order of one megahertz. Hence, the effect of natural line broadening is generally insignificant in LSP processes. Thermal broadening is caused by the Doppler frequency shift of the moving particles at high temperatures, and produces a spectral emission having a Gaussian line shape. Collisional broadening of spectral emissions occurs due to the high pressure of ions and neutrals, and has a Lorentzian line shape. Stark broadening is caused by interaction among electrons or particles with a strong permanent electrical dipole moment and is indicative of the number density of electrons in an area. Stark broadening is also Lorentzian in line shape.

The operating conditions of the laser shock peening process will determine which of these line broadening factors dominates the emission line produced by the LSP system 10. For example, if the LSP system 10 is operating properly, the transparent overlay 24 confines the plasma 32 and the resulting pressure is high in the confined volume. In such a case, the collisional broadening and the Stark broadening dominate the line broadening factors. As a result, the line emission has a substantially Lorentzian line shape. Conversely, if the system is not operating properly, such as in the event of a loss of water confinement over the work piece, the plasma at a high temperature is not confined. In such a case, the line broadening is influenced by both temperature and pressure, such that thermal broadening is a factor and the line broadening has a Voigt line shape, or a convolution between Gaussian and Lorentzian line shapes.

Hence, it is possible to determine if the system is operating properly by comparing the shape of the emission line produced by the LSP system 10 with a Lorentzian curve fit of the emission line. In addition, as will be discussed below, the magnitude of the pressure pulse applied on the work piece may be determined by determining the closeness of the line broadening in the LSP process to a Lorentzian line shape. A Lorentzian line shape conforms to the following equation:

$$y = \frac{a_0}{1 + \left(\frac{x - a_1}{a_2}\right)^2} \quad (1)$$

where: $a_0$ is amplitude of the peak at the wavelength $\lambda_0$;
$a_1$ is the central wavelength $\lambda_0$ of the peak; and
$a_2$ is the width of the spectral emission about wavelength $\lambda_0$.

A Gaussian line shape corresponds to the following equation:

$$y = a_0 \exp\left[-\frac{1}{2}\left(\frac{x - a_1}{a_2}\right)^2\right] \quad (2)$$

where: $a_0$ is amplitude of the peak at the wavelength $\lambda_0$;
$a_1$ is the central wavelength $\lambda_0$ of the peak; and
$a_2$ is the width of the spectral emission about wavelength $\lambda_0$.

Referring generally to FIGS. 3-6, the spectrum analyzer 42 in the illustrated embodiment is adapted to determine the closeness of the line broadening during the LSP process to a Lorentzian line shape and a Gaussian line shape. Conformity of the emission spectrum with the Lorentzian line shape is indicative of proper operation of the LSP process, whereas a lack of conformity with the Lorentzian line shape and conformity with a Gaussian line shape are indicative of an improper operating condition in the LSP process. The spectrum analyzer 42 is adapted to compute a parameter indicative of the closeness of the emission spectrum to a Lorentzian curve fit or a Gaussian curve fit of the emission spectrum and transmit the signal to the process control system 16. Such a parameter may include, for example a coefficient of multiple determination or $R^2$ value. However, other statistical evaluations of the closeness of the fit of the curve to the emission spectrum may be used for comparison. In addition, the spectrum analyzer may compare the coefficient of multiple determination from the Lorentzian curve fit to the coefficient of multiple determination of the Gaussian curve fit. If the coefficient of multiple determination of the Lorentzian curve fit is greater than the coefficient of multiple determination of the Gaussian curve fit, then the line broadening is closer to Lorentzian than Gaussian. The process control system 16 may stop operation of the LSP system 10 or alter the operation of one or more components of the LSP system 10 based on the analysis of the data.

Figure 3:
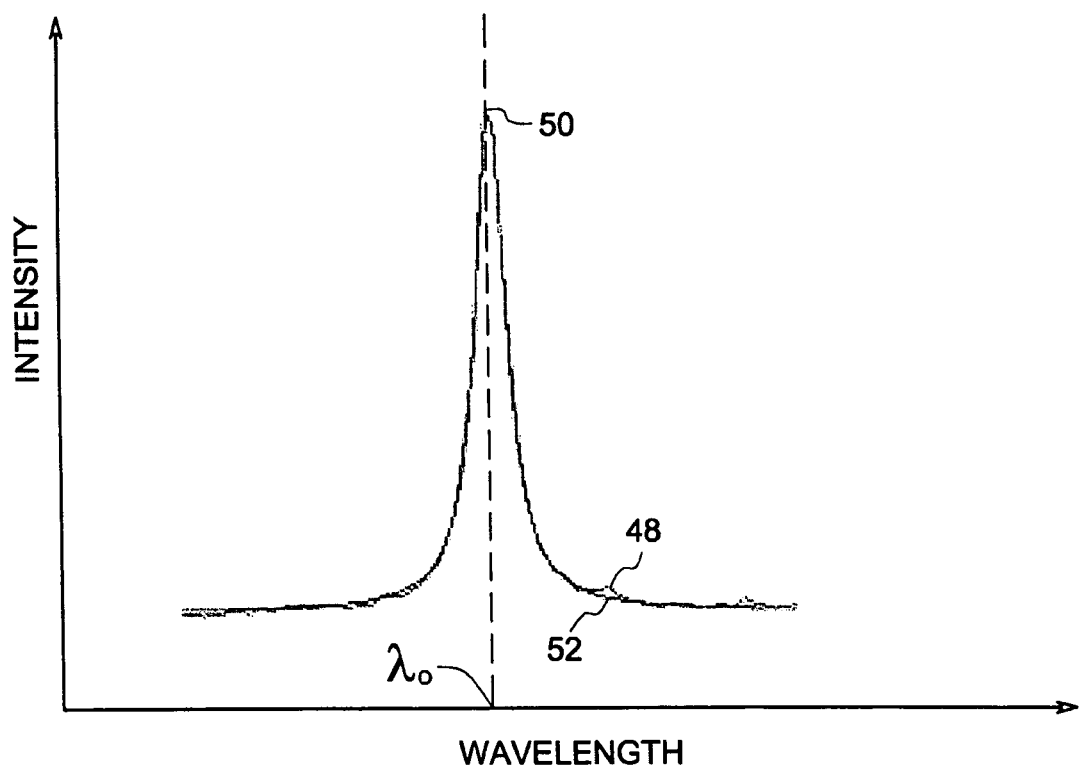
FIG. 3 is a comparative graphical illustration of a line spectrum around a specific wavelength $\lambda_0$ for an LSP process having a transparent layer confinement over a work piece, and a Lorentzian curve fit of the same.
Figure 4:
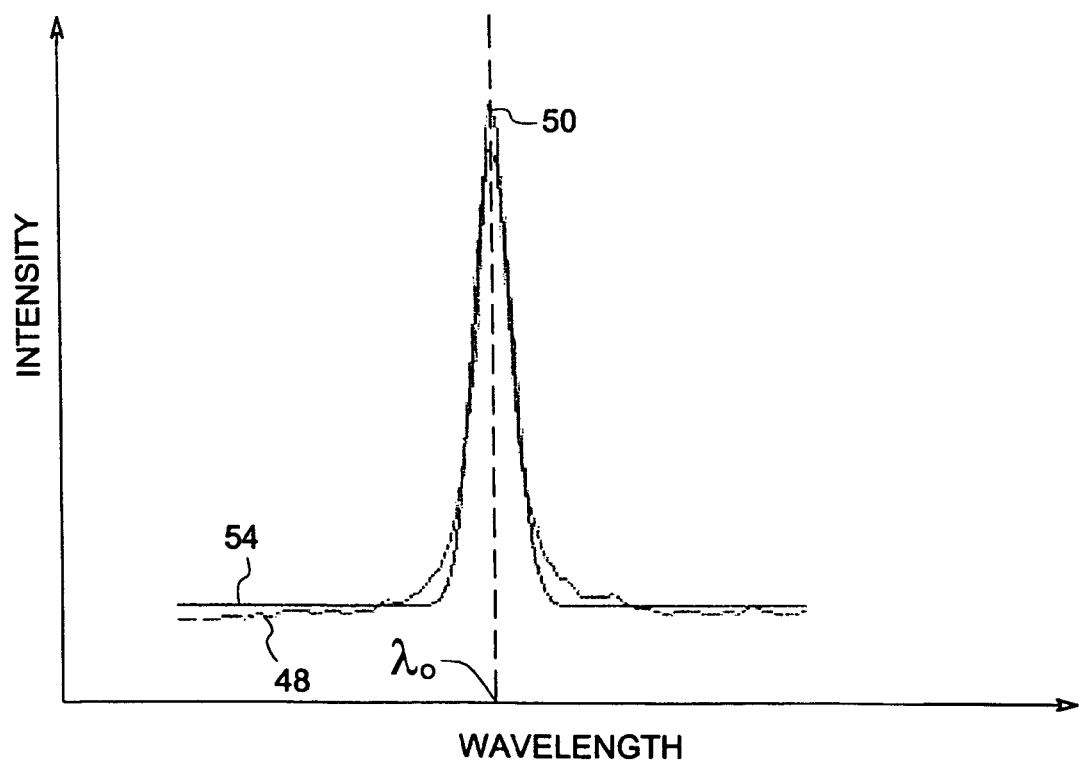
FIG. 4 is a comparative graphical illustration of a line spectrum around a specific wavelength $\lambda_0$ for an LSP process having a transparent layer confinement over a work piece, and a Gaussian curve fit of the same.

Referring generally to FIGS. 3 and 4, an example of an emission spectrum 48 produced by an LSP system that is operating correctly is illustrated. The emission spectrum 48 has a peak 50 at a wavelength ($\lambda_O$). FIG. 3 illustrates a Lorentzian curve fit 52 of the emission line 48 and FIG. 4 illustrates a Gaussian curve fit 54 of the emission line 48. In this embodiment, the intensity of the laser beam 26 and the confinement of the layer of water 24 is sufficient to produce a plasma 32 having a sufficient pressure to enable the collisional broadening and the Stark broadening to dominate the line broadening factors. As a result, the Lorentzian curve 52 illustrated in FIG. 3 exhibits a reasonably high degree of conformity with the emission spectrum 48. Conversely, the emission spectrum 48 does not exhibit a high degree of conformity with the Gaussian curve fit 54 of FIG. 4. Because the emission spectrum 48 exhibits a high degree of conformity with the Lorentzian curve fit 52 and not the Gaussian curve fit 54, the emission spectrum 48 evidences that the LSP system 10 is operating properly, e.g., with the proper water confinement of the plasma.

Figure 5:
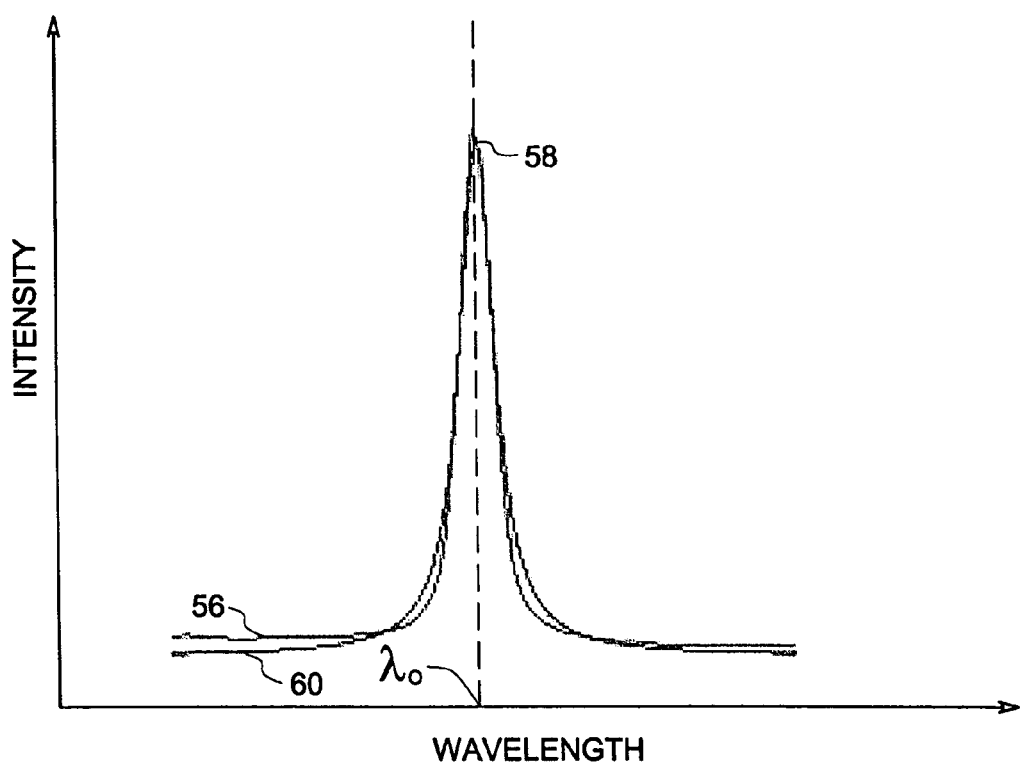
FIG. 5 is a comparative graphical illustration of a line spectrum around a specific wavelength $\lambda_0$ for an LSP process without a transparent layer confinement over a work piece, and a Lorentzian curve fit of the same.
Figure 6:
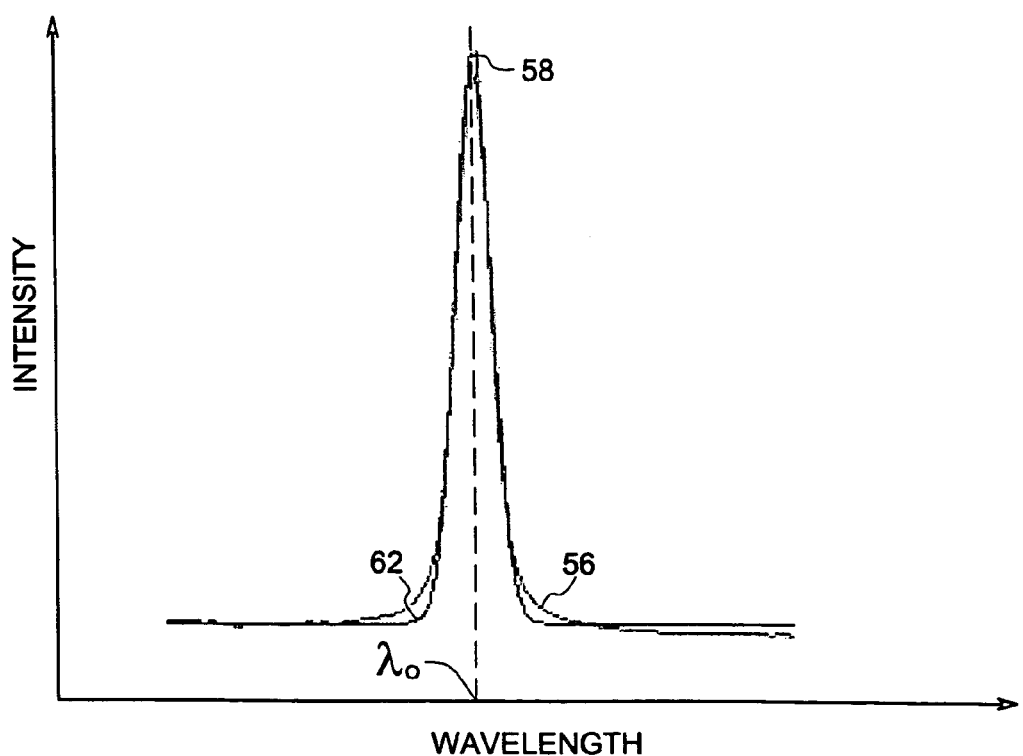
FIG. 6 is a comparative graphical illustration of a line spectrum for an LSP process without a transparent layer confinement over a work piece, and a Gaussian curve fit of the same.

Referring generally to FIGS. 5 and 6, an example of an emission spectrum 56 produced by an LSP system that does not have proper water confinement is illustrated. The emission spectrum 56 has a peak 58 at a wavelength ($\lambda_O$). FIG. 5 illustrates a Lorentzian curve fit 60 of the emission line 48 and FIG. 6 illustrates a Gaussian curve fit 62 of the emission line 48. In this embodiment, the intensity of the laser beam 26 or the confinement of the layer of water 24 does not enable the plasma 32 to achieve a sufficient pressure to enable collisional broadening and the Stark broadening to dominate the line broadening factors. Instead, thermal broadening also influences the line broadening factors. As a result, the Lorentzian curve 60 illustrated in FIG. 5 does not exhibit a reasonably high degree of conformity with the emission spectrum 56. Conversely, the emission spectrum 56 does exhibit some degree of conformity with the Gaussian curve fit 54 of FIG. 6. Because the emission spectrum 48 does not exhibit a high degree of conformity with the Lorentzian curve fit 52 and does exhibit conformity with the Gaussian curve fit 54, the emission spectrum 48 evidences that the LSP system 10 is not operating properly, e.g., the LSP system does not have proper water confinement of the plasma.

Depending on the degree of closeness or conformity of the spectral line broadening with the Lorentzian line shape, the process control system 16 may stop operation of the LSP system 10, generate an alarm, or modify the operation of one or more components of the LSP system 10. For example, the control system 16 may be operable to increase or decrease the laser energy, laser beam diameter at the work piece, the rise time, the pulse width of the laser beam 26, or the thickness of the transparent layer 24 to provide the desired degree of conformity with the Lorentzian line shape.

Figure 7:
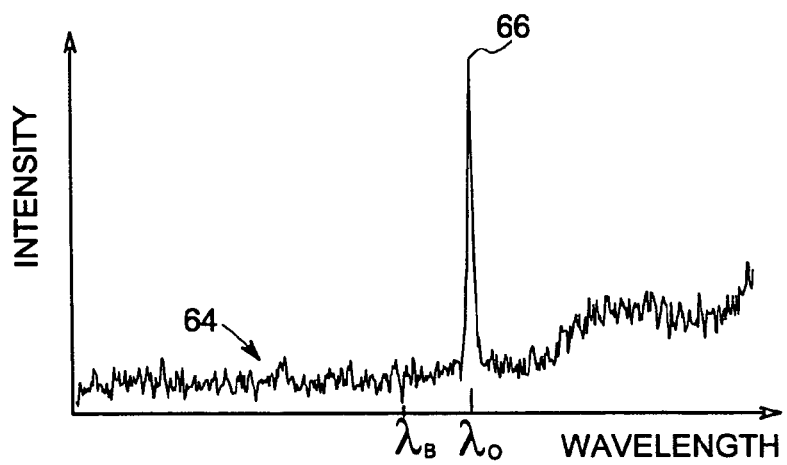
FIG. 7 is a graphical illustration of a line spectrum of radiation produced by laser induced plasma, in case of a burn-through of the opaque layer.
Figure 8:
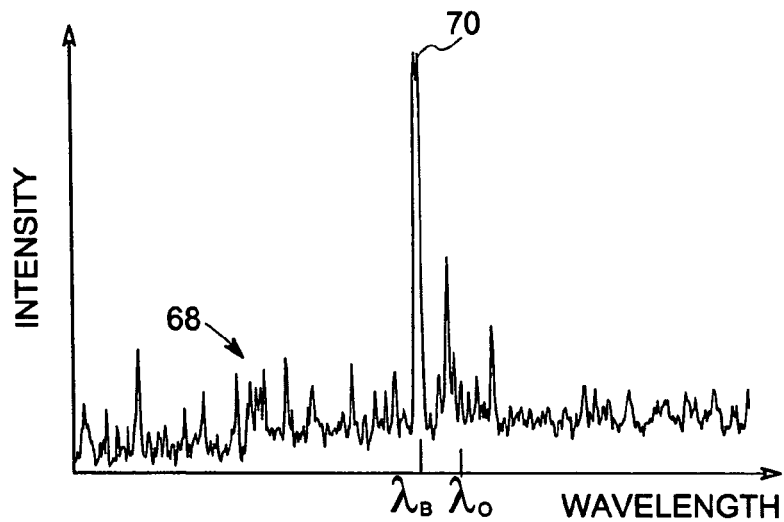
FIG. 8 shows a line spectrum of plasma spectral emission solely from the material of a work piece.
Figure 9:
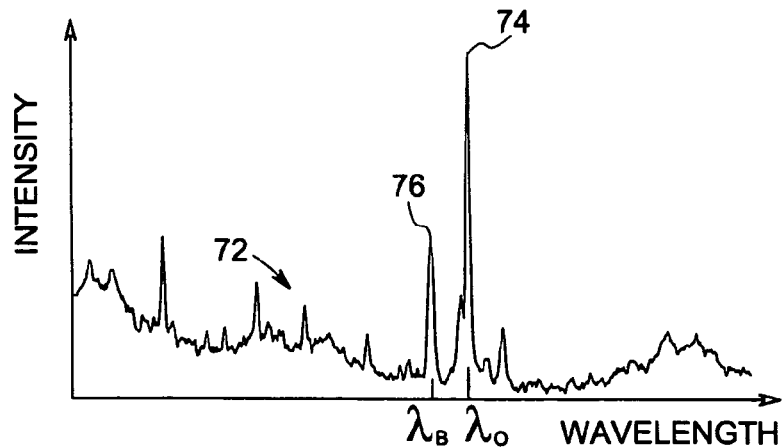
FIG. 9 illustrates a line spectrum produced by a burn-though of an opaque layer.

Referring generally to FIGS. 7-9, the present technique can also be used to detect a failure of the LSP process. In particular, the present technique can be used to detect a burn-through of the opaque layer. In such a case, the opaque layer 22 is vaporized to an extent such that portion of the laser beam 26 is incident directly on the work piece 18, resulting in plasma emission also from the work piece material. As an example, FIG. 7 shows a line spectrum 64 of plasma spectral emission solely from the opaque layer, which has spectral peak at wavelength $\lambda_O$ 66, but no spectral peak at wavelength $\lambda_B$. FIG. 8 shows a line spectrum 68 of plasma spectral emission solely from the material of work piece, which has a characteristic peak 70 at wavelength $\lambda_B$. FIG. 9 illustrates a line spectrum 72 produced by a burn-through of the opaque layer. As illustrated, the line spectrum 72 for the burn-through case comprises significant spectrum spectral peaks 76 and 78, which occur respectively at wavelength $\lambda_B$, which is a characteristic of work piece material, and at wavelength $\lambda_O$, which is a characteristic of the opaque material. A burn-through condition can thus be detected by the presence of an emission peak 76 at a wavelength $\lambda_B$ characteristic of the work piece material, along with the emission peak 74 of the opaque layer, which occurs at wavelength $\lambda_O$. On detection of a burn-through, the control system 16 may shut down the system 10 to enable the problem causing the burn-through to be corrected or may alter the operation of the LSP system to correct this condition.

As can be appreciated, the present technique can be used to analyze every laser shot on the work piece directly and in real time. Therefore, the quality of every laser shot can be guaranteed. Further, the technique described is non-intrusive, as it involves analysis of the laser induced plasma emission, which is a by-product of the LSP process. Moreover, since the method uses line broadening of the plasma emission around an emission peak, and not the absolute signal intensity at an exact wavelength, it is substantially free from environmental influences such as, for example, fluctuations in room light or laser flashlamps, spectrometer absolute wavelength variation, or misalignment of the monitoring system due to system vibration or other causes, amongst others.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A laser shock peening process monitoring method, comprising:
   producing a line spectrum of radiation emitted from a plasma produced by a laser shock peening system;
   converting the line spectrum into a signal representative of the line spectrum;
   converting the signal representative of the line spectrum into a graphical representation of the line spectrum;
   producing a curve fit of the graphical representation of the line spectrum;
   comparing line broadening in the graphical representation of a line spectrum to line broadening in the curve fit of the graphical representation of the line spectrum to establish whether the line spectrum corresponds to a desired line spectrum during the laser shock peening process; and
   controlling the laser shock peening system to alter at least one of laser energy, laser beam diameter at a work piece, rise time, or pulse width of a laser beam produced by the laser shock peening system to produce the plasma based upon comparison.

2. The method as recited in claim 1, wherein producing a curve fit of the graphical representation of the line spectrum comprises producing a Lorentzian curve fit of the line spectrum.

3. The method as recited in claim 2, wherein comparing line broadening in the graphical representation of a line spectrum to line broadening in the curve fit of the graphical representation of the line spectrum comprises visually comparing line broadening in the graphical representation of a line spectrum to line broadening in the Lorentzian curve fit of the graphical representation of the line spectrum.

4. The method as recited in claim 2, wherein comparing line broadening in the graphical representation of a line spectrum to line broadening in the curve fit of the graphical representation of the line spectrum comprises establishing a coefficient of multiple determination of the Lorentzian curve fit of the line spectrum.

5. The method as recited in claim 4, comprising providing a control signal to the laser shock peening sytem when the coefficient of multiple determination corresponding to the Lorentzian curve fit falls below a threshold amount.

6. The method as recited in claim 5, comprising adjusting a laser shock peening system operating parameter based on receipt of the control signal.

7. The method as recited in claim 1, wherein producing a curve fit of the graphical represntation of the line spectrum comprises producing a Gaussian curve fit of the line spectrum.

8. The method as recited in claim 7, wherein comparing line broadening in the graphical representation of a line spectrum to line broadening in the curve fit of the graphical representation of the line spectrum comprises visually comparing line broadening in the graphical representation of a line spectrum to line broadening in the Gaussian curve fit of the graphical representation of the line spectrum.

9. The method as recited in claim 7, wherein comparing line broadening in the graphical representation of a line spectrum to line broadening in the curve fit of the graphical representation of the line spectrum comprises establishing a coefficient of multiple determination of the Gaussian curve fit of the line spectrum.

10. The method as recited in claim 9, comprising providing a control signal to the laser shock peening sytem when the coefficient of multiple determination corresponding to the Gaussian curve fit exceeds a threshold amount.

11. The method as recited in claim 10, comprising adjusting a laser shock peening system operating parameter based on receipt of the control signal.

12. The method as recited in claim 11, wherein adjusting a laser shock peening system operating parameter comprises adjusting the laser shock peening system to alter laser energy.

13. The method as recited in claim 11, wherein adjusting a laser shock peening system operating parameter comprises adjusting the laser shock peening system to alter, laser beam diameter at the work piece, rise time, or pulse width of a laser beam produced by the laser shock peening system to produce the plasma.

14. The method as recited in claim 11, wherein adjusting a laser shock peening system operating parameter comprises adjusting the laser shock peening system to alter rise time of the laser beam.

15. The method as recited in claim 11, wherein adjusting a laser shock peening system operating parameter comprises adjusting the laser shock peening system to alter pulse width of the laser beam produced by the laser shock peening system.

16. The method as recited in claim 11, wherein producing a curve fit of the graphical representation of the line spectrum comprises performing a Lorentzian curve fit and a Gaussian curve fit, and wherein comparing line broadening in the graphical representation of a line spectrum to line broadening in the curve fit of the graphical representation of the line spectrum comprises establishing a coefficient of multiple determination for each of the Lorentzian curve fit and the Gaussian curve fit and comparing them.

* * * * *